United States Patent
Lawrence (10) Patent No.: US 10,968,258 B2
(45) Date of Patent: Apr. 6, 2021

(54) STREPTOCOCCUS SUIS VACCINES TO PROTECT AGAINST REPRODUCTIVE, NURSERY-AGE, AND GROWING PIG DISEASES AND METHODS OF MAKING AND USE THEREOF

(71) Applicant: BOEHRINGER INGELHEIM ANIMAL HEALTH USA INC., Duluth, GA (US)

(72) Inventor: Paulraj Lawrence, Arden Hills, MN (US)

(73) Assignee: BOEHRINGER INGELHEIM ANIMAL HEALTH USA INC., Duluth, GA (US)

( * ) Notice: Subject to any disclaimer, the term of this patent is extended or adjusted under 35 U.S.C. 154(b) by 0 days.

(21) Appl. No.: 16/118,857

(22) Filed: Aug. 31, 2018

(65) Prior Publication Data

US 2019/0241625 A1 Aug. 8, 2019

Related U.S. Application Data

(60) Provisional application No. 62/552,975, filed on Aug. 31, 2017.

(51) Int. Cl.
| | | |
|---|---|---|
| *C07K 14/315* | (2006.01) | |
| *A61K 39/09* | (2006.01) | |
| *A61K 39/39* | (2006.01) | |
| *A61K 39/00* | (2006.01) | |
| *C12Q 1/6869* | (2018.01) | |
| *G16B 30/00* | (2019.01) | |
| *G16B 50/00* | (2019.01) | |
| *C40B 40/08* | (2006.01) | |

(52) U.S. Cl.
CPC .......... *C07K 14/315* (2013.01); *A61K 39/092* (2013.01); *A61K 39/39* (2013.01); *A61K 2039/552* (2013.01); *C12Q 1/6869* (2013.01); *C40B 40/08* (2013.01); *G16B 30/00* (2019.02); *G16B 50/00* (2019.02)

(58) Field of Classification Search
None
See application file for complete search history.

(56) References Cited

U.S. PATENT DOCUMENTS 10,279,031 B2 * 5/2019 Weaver ................. A61K 39/145

FOREIGN PATENT DOCUMENTS

| EP | 2 949 340 A1 | 12/2015 |
| WO | WO 2007/025390 A1 | 3/2007 |
| WO | WO 2014/004361 A1 | 1/2014 |

OTHER PUBLICATIONS

Ellis (Vaccines, W.B. Saunders Company, Chapter 29, 1988, pp. 568-574).*
Boslego et al (Vaccines and Immunotherapy, 1991, Chapter 17).*
Skolnick et al. (Trends in Biotechnology 18: 34-39, 2000).*
Baums, C. G., et. al., 2006. Identification of a novel virulence determinant with serum opacification activity in S. suis. Infect. Immun. 74, 6154-6162.
Baums, C.G., et.al., 2009. S. suis bacterin and subunit vaccine immunogenicities and protective efficacies against serotypes 2 and 9.Clin Vacc Immunol. 2, 200-208.
Berthelot-Herault, F., et. al., 2005. Dilemma of virulence of S. suis: Canadian isolate 89-1591 characterized as a virulent strain using a standardized experimental model in pigs. Can. J. Vet. Res. 69, 236-240.
Chabot-Roy, G., Willson, P., Segura, M., Lacouture, S., Gottschalk, M., 2006. Phagocytosis and killing of Sreptococcus suis by porcine neutrophils. Microb. Pathog. 41, 21-32.
Edholm V, et al.: Fratricide in Streptococcus pneumoniae: contributions and role of the cell wall hydrolases CbpD, LytA and LytC. Microbiology., 2009, 155:2223-2234.
Gottschalk M, et.a.,. Characterization of six new capsular types (23 through 28) of Streptococcus suis. J Clin Microbiol. Nov. 29, 1991(11):2590-4.
Higgins R, Gottschalk M, Boudreau M, Lebrun A, Henrichsen J: Description of six new capsular types (29-34) of Streptococcus suis. J Vet Diagn Invest., 1995, 7:405-406.
Higgins R, Gottschalk M Distribution of Streptococcus suis capsular types in 1998. Can Vet J. Apr. 1999;40(4):277.
Higgins, R., Gottschalk, M., 2006. Streptococcal diseases. In: Straw, B.E., et. al., (Eds), Diseases of Swine. Blackwell Publishing, pp. 769-783
Hill JE, et al.: Biochemical analysis, cpn60 and 16S rDNA sequence data indicate that S. suis serotypes 32 and 34, from pigs, are S. orisratti. Vet Microbiol., 2005, 107:63-69.
Hu P, Yang M, Zhang A, Wu J, Chen B, Hua Y, Yu J, Chen H, Xiao J, Jin M. Complete genome sequence of Streptococcus suis serotype 3 strain ST3, J. Bacteriol. 193 (2011) 3428-3429.

(Continued)

*Primary Examiner* — Robert A Zeman
(74) *Attorney, Agent, or Firm* — Suzanne Seavello Shope; John Ezcurra (57) ABSTRACT

The present invention provides *S. suis* strains that elicit an immune response in animal *S. suis*, compositions comprising said strains, methods of vaccination against *S. suis*, and kits for use with such methods and compositions. The invention further provides a comprehensive, unambiguous method of capsular typing based on whole genome sequencing and bioinformatics. This capsular typing approach can accurately identify serotypes even when strains possess novel capsular loci and can be used to determine which strains to include when formulating vaccines, including herd specific vaccines.

10 Claims, 6 Drawing Sheets

Specification includes a Sequence Listing.

(56) References Cited

OTHER PUBLICATIONS

Hu P, Yang M, Zhang A, Wu J, Chen B, Hua Y, Yu J, Xiao J, Jin M. Complete genome sequence of *Streptococcus suis* serotype 14 strain JS14, J. Bacteriol. 193 (2011) 2375-2376

Okura M, et. al., Genetic analysis of capsular polysaccharide synthesis gene clusters from all serotypes of *Streptococcus suis*: potential mechanisms for generation of capsular variation. Appl Environ Microbiol. Apr. 2013;79 (8):2796-806.

Pan Z, et al.: Novel variant serotype of *S. suis* isolated from piglets with meningitis. Appl. Environ. Microbiol., 2015, 81:976-985.

Quessy, S., et. al., 1995. Discrimination of virulent and avirulent *Streptococcus suis* capsular type 2 isolates from different geographical origins. Infect. Immun. 63, 1975-1979.

Qiu Z, et al.: Novel capsular polysaccharide loci and new diagnostic tools for high-throughput capsular gene typing in *S. suis*. Appl. Environ. Microbiol., 2016, 21:7102-7112.

Smith, H.E., et. al., 1999. Identification and characterization of the cps locus of *S. suis* serotype 2: the capsule protects agnst phagocytosis and is an important virulence factor. Infect. Immun 67, 1750-56.

Smith HE, et.al., The cps genes of *Streptococcus suis* serotypes 1, 2, and 9: development of rapid serotype-specific PCR assays. J Clin Microbiol 1999, 37(10):3146-3152.

Tien LHT, et al: Reappraisal of the taxonomy of *S. suis* serotypes 20, 22, 26, and 33 based on DNA-DNA homology and sodA and recN phylogenies. Vet Microbiol., 2013, 162:842-849.

Vecht, U., Wisselink, H.J., Jellema, M.L., Smith, H.E., 1991. Identification of two proteins associated with virulence of *S. suis* type 2. Infect. Immun. 59, 3156-3162.

Vecht, U., et.al., 1992. Virulence of *Streptococcus suis* type 2 strains in newborn germfree pigs depends on phenotype. Infect. Immun. 60, 550-556.

Wang K, Fan W, Cai L, Huang B, Lu C. Genetic analysis of the capsular polysaccharide synthesis locus in 15 *S. suis* serotypes. FEMS Microbiol Lett. Nov. 2011;324(2):117-24.

Wei Z, et.al., Characterization of *S. suis* isolates from the diseased pigs in China between 2003 and 2007. Vet Microbiol 2009, 137(1-2):196-201.

Zhang A, et. al., Comparative genomic analysis of *S. suis* reveals significant genomic diversity among different serotypes. Oct. 25, 2011;12:523.

Zheng H, et al.: Eight novel capsular polysaccharide synthesis gene loci identified in nontypeable *Streptococcus suis* isolates. Appl. Environ. Microbiol., 2015, 81:4111-4119.

Brockmeier, S. L., et. al., 2017, Use of proteins identified through a functional genomic screen to develop a protein subunit vaccine that provides significant protection against virulent *Streptococcus suis* in pigs. Infection and Immun. vol. 86, No. 3.

Database Protein Online XP0002786302, "nucleotide sugar synthetase-like protein [*Streptococcus suis*]", Aug. 10, 2015; retrieved from NCBI, accession No. WP_050571188.

Database Protein Online XP0002786303, "Glycosyltransferase family 2 protein [*Streptococcus suis*]", Jul. 4, 2017; retrieved from NCBI, accession No. WP_044676816.

Database Protein Online XP0002786304, "accessory Sec system protein translocase subunit SecY2 [*Streptococcus suis*]", Nov. 29, 2015; retrieved from NCBI, accession No. WP_044766479.

Givens D., et. al., Aug. 1, 2008, Infectious causes of embryonic and fetal mortality. Theriogenology. vol. 70, No. 3, pp. 270-285.

Segura M., et. al., Oct. 15, 2015. *Streptococcus suis* vaccines: candidate antigens and progress. Expert Review of Vaccines, vol. 14, No. 12, pp. 1587-1608.

\* cited by examiner

| Isolate | Tissue of Origin | Cps 27% Locus Coverage | Cps 12% Locus Coverage |
|---|---|---|---|
| 17SP1 | Vaginal | 40.6 | 42.5 |
| 17SP2 | Vaginal | 39.4 | 38.6 |
| 17SP3 | Liver | 28.2 | - |
| 17SP4 | Spleen | 23.9 | - |
| 17SP5 | Nasal Swab | 42.5 | - |
| 16HCP1 | Heart | 66.0 | - |
| 16HCP2 | Brain | 88.2 | - |
| 17NPL1 | Laryngeal Swab | 43.1 | - |

| Isolate | PCR | WGS | Agglutination |
|---|---|---|---|
| 14CF1 | Not Typeable | 3 (85%) | Not Typeable |
| 14CF2 | Not Typeable | 10 (83.8%) | Not Typeable |
| 14CF3 | Not Typeable | 3 (85.8%) | Not Typeable |
| 14CF4 | 2 | 1/2 (96.7%) | 2 |
| 14CF5 | 9 | 9 (59.4%) | 9 |
| 14CF6 | Not Typeable | 3 (84.5%) | Not Typeable |
| 14CF7 | Not Typeable | 3 (99.8%) | 3 |
| 14CF8 | 7 | 7 (99.6%) | 7 |
| 14CF9 | Not Typeable | 23 (72.5%) | 23 |
| 14CG1 | 2 | 2 (88.9%) | 1/2 |
| 14CG2 | 2 | 2 (93.0%) | 1/2 |
| 14CG3 | 2 | 2 (93.0%) | 1/2 |
| 14CG4 | 2 | 2 (93.0%) | 1/2 |
| 14CG5 | 2 | 2 (93.0%) | 1/2 |

STREPTOCOCCUS SUIS VACCINES TO PROTECT AGAINST REPRODUCTIVE, NURSERY-AGE, AND GROWING PIG DISEASES AND METHODS OF MAKING AND USE THEREOF

CROSS-REFERENCE TO RELATED APPLICATIONS

This application claims priority to U.S. provisional application No. 62/552,975, filed 31 Aug. 2017, and incorporated herein by reference in its entirety.

INCORPORATION BY REFERENCE

Any foregoing applications and all documents cited therein or during their prosecution ("application cited documents") and all documents cited or referenced in the application cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. Citation or identification of any such document in this application is not an admission that such document is available as prior art to the present invention and does not reflect any view of the validity, patentability and/or enforceability of such cited patent documents. All sequences referenced herein by GenBank Accession numbers are herein incorporated by reference in their entirety, and said sequences are as set forth in GenBank at as of the filing date of the present application.

FIELD OF THE INVENTION

The present invention relates generally to bacterial vaccines, particularly those providing safe, and effective protection to porcines against reproductive, nursery-age, and growing pig disease caused by a newly identified strain of *Streptococcus suis*. The invention further relates to methods of producing the bacteria, and to the identification of nucleic acid variations that are associated with a novel capsular structure, the cbpD gene, and an alternative secretory pathway which may confer upon these strains a unique ability to colonize the vaginal tract and provide a competitive advantage against other strains. The invention accordingly relates to immunogenic or vaccine compositions comprising the bacteria of the invention; e.g., live, attenuated or killed bacteria. The invention further relates to methods for preparing and/or formulating such compositions. The invention further relates to a comprehensive, unambiguous method of capsular typing based on whole genome sequencing and bioinformatics. This capsular typing approach can accurately identify serotypes even when strains possess novel capsular loci and can be used to determine which strains to include when formulating vaccines, including herd specific vaccines.

STATEMENT REGARDING SEQUENCE LISTING

The Sequence Listing associated with this application is provided in text format in lieu of a paper copy, and is hereby incorporated by reference into the specification. The name of the text file containing the Sequence Listing is MER 17-323 ST25.txt. The text file is 1,565 KB; it was created on 30 Aug. 2018; and it is being submitted electronically via EFS-Web, concurrent with the filing of the specification.

BACKGROUND OF THE INVENTION

*Streptococcus suis* is a Gram positive cocci that predominantly colonizes pigs. While the adult pigs serve as asymptomatic carries, it can cause fatal meningitis, septicemia arthritis and bronchopneumonia in piglets. Adult pigs usually carry *S. suis* as commensal in their tonsillar crypts and upper respiratory tracts, but bacteria have also been isolated from the gastrointestinal and genital tracts. Almost all the adult pigs serve as reservoirs for *S. suis* and this pathogen affects pig industries worldwide.

*Streptococcus suis* can also cause abortions in infected sows (Givens M D, Marley M S: Infectious causes of embryonic and fetal mortality. Theriogenology, 2008, 70:270-285). Based on agglutination tests, 35 different serotypes of *S. suis* have been identified to date (Higgins R, Gottschalk M, Boudreau M, Lebrun A, Henrichsen J: Description of six new capsular types (29-34) of *Streptococcus suis*. J Vet Diagn Invest., 1995, 7:405-406); however, recent work suggests that six of the original serotypes are new species (Hill J E, et al.: Biochemical analysis, cpn60 and 16S rDNA sequence data indicate that *Streptococcus suis* serotypes 32 and 34, isolated from pigs, are *Streptococcus orisratti*. Vet Microbiol., 2005, 107:63-69; Tien L H T, et al: Reappraisal of the taxonomy of *Streptococcus suis* serotypes 20, 22, 26, and 33 based on DNA-DNA homology and sodA and recN phylogenies. Vet Microbiol., 2013, 162:842-849). *S. suis* is a common resident of the reproductive tract of sows. However, it is also an opportunistic pathogen and is occasionally isolated from sows exhibiting symptoms of vaginal discharge and endometritis (Torremorrell M. Bacterial, rickettsial, protozoal, and fungal causes of infertility and abortion in swine: In Youngquist R S, Threlfall W R, editors. Current therapy in large animal theriogenology. 2nd ed., St. Louis: Elsevier; 2007, 794-801).

The first description of streptococcal infection is attributed to the Austrian surgeon, Theodor Billroth in 1874 (Billroth, 1874; Billroth, 1877). Additional refinement of the name *Streptococcus* came from Friedrich Julius Rosenbach in 1884, who examined bacteria isolated from suppurative lesions, and began naming species (Evans, 1936). The introduction of blood agar plates by Hugo Schottmuller in 1903 was an important step forward for the differentiation of streptococci (Schottmuller, 1903; Becker, 1916). In 1933, Lancefield used surface antigen differences among various streptococci to further subdivide them into groups designated by the letters A through X (Kohler, 2008). The strains from human diseases were classified as Group A; the strains from bovine and dairy sources as Group B; the strains from a variety of animal sources as Group C; and so forth. For epidemiological studies, the determination of the T-antigens by slide agglutination was introduced by Fred Griffith of London in 1934 (Griffith, 1934) (Kohler, 1974). More recent descriptions of the "present state of species within the genus *Streptococcus* and *Enterococcus*" by Kohler (Kohler, 2007), and a "phylogenomic analysis of genome evolution in the genus *Streptococcus*" by Richards et al. (Richards, et al., 2014) provide important new overviews of the genus *Streptococcus*. Complete citations can be found at ncbi.nlm.nih.gov/books/NBK333430.

With respect to Streptococcal animal strains, there has been much less progress in classification. There are 35 known serotypes of *S. suis* based on the antigenic differences of the capsular polysaccharide. Some researchers consider that there are only 29 unique serotypes, excluding numbers 20, 22, 26, 33, 32 and 34 (FIG. 7). Serotype 2 (ST2) is most prevalent in North America and Europe followed by serotypes 3 and ½.

The two known methods of identification described above each only identify a portion of the 35 known species (FIG. 6). Thus there has been a long-felt in animal husbandry for a more comprehensive type of serotyping. The newly derived method described herein fills this need.

Whole cells and numerous *S. suis* proteins have been investigated as potential vaccine candidates. Immunization with a wild type bacterin completely protected against challenge with the homologous serotype while non-encapsulated mutant failed to afford protection [Wisselink et al., 2002]. In a study conducted by Li et al, recombinant SAO (*S. suis* surface protein) in combination with Quil A protected against *S. suis* serotype 2 disease in pigs. Intramuscular immunization with SAO elicited significant humoral antibody responses, but were predominantly IgG2. Recombinant SAO immunization also induced opsonophagocytic antibodies [Li, Yuanyi, et al. "Immunization with Recombinant Sao Protein Confers Protection against *Streptococcus Suis* Infection." *Clinical and Vaccine Immunology*, American Society for Microbiology, 1 Aug. 2007, cvi.asm.org/content/14/8/937]. Immunization of piglets with purified suilysin from *S. suis* strain P1/7 (serotype 2), increased neutralizing antibody titers suggesting that SLY might function as protective antigen [Jacobs, A. A. C., et al. "Protection of Experimentally Infected Pigs by Suilysin, the Thiol-Activated Haemolysin of *Streptococcus suis." Veterinary Record*, British Medical Journal Publishing Group, 7 Sep. 1996, veterinaryrecord.bmj.com/content/139/10/225]. However, none of these experiments used heterologous serotypes to challenge pigs vaccinated with these antigens. In a study by Baums et al, *S. suis*, serotype 2 bacterin induced protective immunity against homologous challenge. In contrast, the protective efficacy of the MAP subunit vaccine was low, although MAP immunization resulted in high serum IgG2 titers against MRP and SAO. Importantly, immunization with bacterin but not with MAP induced opsonizing antibody titers against the serotype 2 strain, and these antibody titers were found to correlate with protection. However, after absorption with a non-encapsulated isogenic mutant, the sera from bacterin-immunized piglets failed to facilitate neutrophil killing, indicating that antibodies directed against capsule may not have been essential for opsonophagocytosis [Baums, Christoph Georg, et al. "*Streptococcus Suis* Bacterin and Subunit Vaccine Immunogenicities and Protective Efficacies against Serotypes 2 and 9." *Clinical and Vaccine Immunology*, American Society for Microbiology, 1 Feb. 2009, cvi.asm.org/content/16/2/200]. Furthermore, induction of opsonizing antibodies against serotype 9 was not detectable in the group receiving bacterin or in the group receiving the MAP vaccine, resulting in low protection against serotype 9 strains.

Lack of an effective vaccine against *S. suis* reproductive, nursery-age, and growing pig disease is a new problem in modern swine production.

SUMMARY OF THE INVENTION

Thus, it a primary object of the instant disclosure to provide a safe and effective *S. suis* vaccine against reproductive, nursery-age, and growing pig diseases.

The invention further provides methods for inducing an immunological (or immunogenic) or protective response against *S. suis* reproductive, nursery-age, or growing pig/swine diseases. An object of this invention is to provide vaccines as well as methods for treatment and prophylaxis of reproductive, nursery-age, and growing pig disease by a new strain of *S. suis* which has been identified as an abortifacient agent.

The present invention further relates to immunogenic regions of new strains of *S. suis*, which provide safe, and effective protective immunity against reproductive disease. Relative to a parent *S. suis* strain, the strains may have one or more capsular variants, whose presence is associated with a unique ability to colonize the vaginal tract and provide a competitive advantage against other strains.

The invention accordingly relates to immunogenic or vaccine compositions comprising the bacteria of the invention; e.g., live, attenuated or killed bacteria.

In a particular embodiment, the newly discovered strains have a highly divergent serotype with some similarity to serotypes 27 and 12 (FIG. 3).

According to one particular embodiment, the strains may have "alternative forms of genes", which are defined herein as "alleles", relative to their parent *S. suis* strain. In an embodiment, the alternative alleles are responsible for reduced virulence.

According to another aspect, the present invention relates to two operons that contribute to the pathology associated with these strains by serving as host-cell adhesins. The first is an alternative secretory operon the second operon is a set of capsular genes that are involved in phosphorylcholine metabolism.

According to another aspect, the newly identified strains possess a lytic choline binding protein D homolog (cbpD). This protein functions differently in strain with a competent export system.

The invention therefore further relates to methods for preparing and/or formulating such compositions; e.g., culturing or growing or propagating the bacteria on or in suitable medium, harvesting the bacteria, optionally killing, inactivating or attenuating the bacteria, and optionally admixing the bacteria with a suitable veterinarily or pharmaceutically acceptable carrier, excipient, diluent or vehicle and/or an adjuvant and/or stabilizer. Thus, the invention also relates to the use of the bacteria in formulating such compositions.

Also disclosed are methods for preventing or treating *S. suis* reproductive, nursery-age, and growing pig/swine diseases, or reproductive, nursery-age, and growing pig/swine disease state(s) caused by *S. suis*, comprising administering the bacteria, which can be live, killed, attenuated, or inactivated, or an immunogenic region thereof; or a composition comprising the live, killed, attenuated, or inactivated bacteria, or an immunogenic region of the bacteria to animals in need thereof.

It is another object of the invention to provide a comprehensive, unambiguous method of capsular typing based on whole genome sequencing and bioinformatics that can accurately identify serotypes even when strains possess novel capsular loci.

It is a further object of the present invention to use this method of capsular typing to determine which strains to include when formulating vaccines, including herd specific vaccines.

In one embodiment, the vaccines further comprise an adjuvant. The adjuvant may be any substance which increases and/or augments the elicited immune response, as compared to vaccine alone. Mucosal adjuvants, including chitosans and derivatives thereof, are particularly useful for the disclosed oral vaccines.

In a further embodiment the present invention comprises using this method of capsular typing to determine which strains to include when formulating vaccines, including herd specific vaccines. It is another object of the invention to provide kits comprising live, killed, attenuated, or inactivated bacteria, or an immunogenic region of the bacteria of at least the newly identified *S. suis* strain and instructions for use to prevent or treat reproductive, nursery-age, and growing pig/swine disease.

It is another object of the invention to provide kits for performing metagenomics analysis of new strains of *S. suis*.

It is another object of the invention to provide kits for preparing vaccines to any serotype discovered in metagenomics analysis.

These and other embodiments are disclosed or are obvious from, and encompassed by, the following Detailed Description.

BRIEF DESCRIPTION OF THE DRAWINGS

A full and enabling disclosure of the present invention, including the best mode thereof, to one of ordinary skill in the art, is set forth more particularly in the remainder of the specification, including reference to the accompanying figures, wherein:

FIG. 2 shows metagenomic analysis—representative phylum level results from vaginal swabs; 2a in normal sows and 2b in aborting sows with vaginal discharge.

DETAILED DESCRIPTION OF THE INVENTION

The present invention provides nucleotide sequences and genes involved in identifying *Streptococcus suis* (*S. suis*), products (e.g., proteins, antigens, immunogens, epitopes) encoded by the nucleotide sequences, methods for producing such nucleotide sequences, products, micro-organisms, and uses therefor, such as for preparing vaccine or immunogenic compositions or for eliciting an immunological or immune response or as a vector, e.g., as an expression vector (for instance, an in vitro or in vivo expression vector).

In particular, the present invention encompasses new *S. suis* strains and vaccines comprising the same, which elicit an immunogenic response in an animal, particularly the *S. suis* strains that elicit, induce or stimulate a response in a porcine. The protocols of the invention protect the animal from *S. suis* and/or prevent disease progression in an infected animal.

In an embodiment, the strains comprise nucleic acid sequences having at least 70%, at least 80%, or at least 90% identity to a sequences as set forth in SEQ ID NO comprising the nucleotides as set forth in SEQ ID NO: 1, 3, 5, 7, 9, 11, 13, 15, 17, 19, 21, 23, 25, 27, 29, or 31; or a conservative variant (or at least 70%, at least 80%, or at least 90% identity) of the polypeptide having the sequence as set forth in SEQ ID NO:2, 4, 6, 8, 10, 12, 14, 16, 18, 20, 22, 24, 26, 28, 30 or 32; or a combination thereof.

In an embodiment, the strains comprise nucleic acid sequences having at least 70%, at least 80%, or at least 90% identity to the nucleotides as set forth in SEQ ID NOs:3, 7, and 11, or combinations thereof. In another embodiment, the *S. suis* strains comprise nucleic acids encoding peptides having a concervative variant (or at least 70%, at least 80%, or at least 90% identity) of the sequence as set forth in SEQ ID NOs:4, 8, 12 or combinations thereof.

In another aspect, the novel *S. suis* strains are formulated into safe, effective vaccine against *S. suis* and infections/diseases caused by *S. suis*.

In an embodiment, the *S. suis* vaccines further comprise an adjuvant. In a particular embodiment, the adjuvant is a mucosal adjuvant, such as chitosan, methylated chitosan, trimethylated chitosan, or derivatives or combinations thereof.

In an embodiment, the adjuvant comprises whole bacteria and/or viruses, including *H. parasuis, clostridium*, swine influenza virus (SIV), porcine circovirus (PCV), porcine reproductive and respiratory syndrome virus (PRRSV), *Mannhemia, Pasteurella, Histophious, Salmonella, Escherichia coli*, or combinations and/or variations thereof. In several embodiments, the adjuvant increases the animal's production of IgM, IgG, IgA, and/or combinations thereof.

By "antigen" or "immunogen" or "immunogenic region" means a substance that induces a specific immune response in a host animal. The antigen may comprise a whole organism, killed, or live; a subunit or portion of an organism; a recombinant vector containing an insert with immunogenic properties; a piece or fragment of DNA capable of inducing an immune response upon presentation to a host animal; a polypeptide, an epitope, a hapten, or any combination thereof. Alternately, the immunogen or antigen may comprise a toxin or antitoxin.

The terms "protein", "peptide", "polypeptide" and "polypeptide fragment" are used interchangeably herein to refer to polymers of amino acid residues of any length. The polymer can be linear or branched, it may comprise modified amino acids or amino acid analogs, and it may be interrupted by chemical moieties other than amino acids. The terms also encompass an amino acid polymer that has been modified naturally or by intervention; for example disulfide bond formation, glycosylation, lipidation, acetylation, phosphorylation, or any other manipulation or modification, such as conjugation with a labeling or bioactive component.

The term "immunogenic or antigenic polypeptide" as used herein includes polypeptides that are immunologically active in the sense that once administered to the host, it is able to evoke an immune response of the humoral and/or cellular type directed against the protein. Preferably the protein fragment is such that it has substantially the same immunological activity as the total protein. Thus, a protein fragment according to the invention comprises or consists essentially of or consists of at least one epitope or antigenic determinant. An "immunogenic" protein or polypeptide, as used herein, includes the full-length sequence of the protein, analogs thereof, or immunogenic fragments thereof. By "immunogenic fragment" is meant a fragment of a protein which includes one or more epitopes and thus elicits the immunological response described above. Such fragments can be identified using any number of epitope mapping techniques, well known in the art. See, e.g., Epitope Mapping Protocols in Methods in Molecular Biology, Vol. 66 (Glenn E. Morris, Ed., 1996). For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al., 1984; Geysen et al., 1986. Similarly, conformational epitopes are readily identified by determining spatial conformation of amino acids such as by, e.g., x-ray crystallography and 2-dimensional nuclear magnetic resonance. See, e.g., Epitope Mapping Protocols, supra. Methods especially applicable to the proteins of T. parva are fully described in PCT/US2004/022605 incorporated herein by reference in its entirety.

The term "field strains" as used herein includes samples collected in any area where sows and growing pigs are found, such as in a farm environment or in the wild.

As discussed herein, the invention encompasses active fragments and variants of the antigenic polypeptide. Thus, the term "immunogenic or antigenic polypeptide" further contemplates deletions, additions and substitutions to the sequence, so long as the polypeptide functions to produce an immunological response as defined herein. The term "conservative variation" denotes the replacement of an amino acid residue by another biologically similar residue, or the replacement of a nucleotide in a nucleic acid sequence such that the encoded amino acid residue does not change or is another biologically similar residue. In this regard, particularly preferred substitutions will generally be conservative in nature, i.e., those substitutions that take place within a family of amino acids. For example, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cystine, serine, threonine, tyrosine. Phenylalanine, tryptophan, and tyrosine are sometimes classified as aromatic amino acids. Examples of conservative variations include the substitution of one hydrophobic residue such as isoleucine, valine, leucine or methionine for another hydrophobic residue, or the substitution of one polar residue for another polar residue, such as the substitution of arginine for lysine, glutamic acid for aspartic acid, or glutamine for asparagine, and the like; or a similar conservative replacement of an amino acid with a structurally related amino acid that will not have a major effect on the biological activity. Proteins having substantially the same amino acid sequence as the reference molecule but possessing minor amino acid substitutions that do not substantially affect the immunogenicity of the protein are, therefore, within the definition of the reference polypeptide. All of the polypeptides produced by these modifications are included herein. The term "conservative variation" also includes the use of a substituted amino acid in place of an unsubstituted parent amino acid provided that antibodies raised to the substituted polypeptide also immunoreact with the unsubstituted polypeptide.

The term "epitope" refers to the site on an antigen or hapten to which specific B cells and/or T cells respond. The term is also used interchangeably with "antigenic determinant" or "antigenic determinant site". Antibodies that recognize the same epitope can be identified in a simple immunoassay showing the ability of one antibody to block the binding of another antibody to a target antigen.

An "immunological response" to a composition or vaccine is the development in the host of a cellular and/or antibody-mediated immune response to a composition or vaccine of interest. Usually, an "immunological response" includes but is not limited to one or more of the following effects: the production of antibodies, B cells, helper T cells, and/or cytotoxic T cells, directed specifically to an antigen or antigens included in the composition or vaccine of interest. Preferably, the host will display either a therapeutic or protective immunological response such that resistance to new infection will be enhanced and/or the clinical severity of the disease reduced. Such protection will be demonstrated by either a reduction or lack of symptoms and/or clinical disease signs normally displayed by an infected host, a quicker recovery time and/or a lowered viral titer in the infected host.

The immunological response against S. suis reproductive, nursery-age, and growing pig diseases can be generated by administering the bacteria, which can be live, killed, attenuated, or inactivated, or administering an immunogenic region thereof; or a composition comprising the live, killed, attenuated, or inactivated bacteria, or an immunogenic region of the bacteria to animals.

By "animal" is intended mammals, birds, and the like. Animal or host as used herein includes mammals and human. The animal may be selected from the group consisting of equine (e.g., horse), canine (e.g., dogs, wolves, foxes, coyotes, jackals), feline (e.g., lions, tigers, domestic cats, wild cats, other big cats, and other felines including cheetahs and lynx), ovine (e.g., sheep), bovine (e.g., cattle), porcine (e.g., pig, swine), avian (e.g., chicken, duck, goose, turkey, quail, pheasant, parrot, finches, hawk, crow, ostrich, emu and cassowary), primate (e.g., prosimian, tarsier, monkey, gibbon, ape), ferrets, seals, and fish. The term "animal" also includes an individual animal in all stages of development, including newborn, embryonic and fetal stages.

Unless otherwise explained, all technical and scientific terms used herein have the same meaning as commonly understood by one of ordinary skill in the art to which this disclosure belongs. The singular terms "a", "an", and "the" include plural referents unless context clearly indicates otherwise. Similarly, the word "or" is intended to include "and" unless the context clearly indicate otherwise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

Compositions

The present invention relates to a S. suis vaccine or composition which may comprise an S. suis strain and a pharmaceutically or veterinarily acceptable carrier, excipient, or vehicle, which elicits, induces or stimulates a response in an animal.

The term "nucleic acid" and "polynucleotide" refers to RNA or DNA that is linear or branched, single or double stranded, or a hybrid thereof. The term also encompasses RNA/DNA hybrids. The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes and primers. A polynucleotide may comprise modified nucleotides, such as methylated nucleotides and nucleotide analogs, uracyl, other sugars and linking groups such as fluororibose and thiolate, and nucleotide branches. The sequence of nucleotides may be further modified after polymerization, such as by conjugation, with a labeling component. Other types of modifications included in this definition are caps, substitution of one or more of the naturally occurring nucleotides with an analog, and introduction of means for attaching the polynucleotide to proteins, metal ions, labeling components, other polynucleotides or solid support. The polynucleotides can be obtained by chemical synthesis or derived from a microorganism.

The term "gene" is used broadly to refer to any segment of polynucleotide associated with a biological function. Thus, genes include introns and exons as in genomic sequence, or just the coding sequences as in cDNAs and/or the regulatory sequences required for their expression. For example, gene also refers to a nucleic acid fragment that expresses mRNA or functional RNA, or encodes a specific protein, and which includes regulatory sequences. "Gene" shall also encompass both coding and non-coding sequences (i.e. upstream and downstream regulatory sequences, promoters, 5'/3' UTR, introns, and exons). Where reference to only a gene's coding sequence is intended, the term "gene's coding sequence" or "CDS" will be used interchangeably throughout this disclosure.

An "isolated" biological component (such as a nucleic acid or protein or organelle) refers to a component that has been substantially separated or purified away from other biological components in the cell of the organism in which the component naturally occurs, for instance, other chromosomal and extra-chromosomal DNA and RNA, proteins, and organelles. Nucleic acids and proteins that have been "isolated" include nucleic acids and proteins purified by standard purification methods. The term also embraces nucleic acids and proteins prepared by recombinant technology as well as chemical synthesis.

The term "conservative variation" denotes the replacement of an amino acid residue by another biologically similar residue, or the replacement of a nucleotide in a nucleic acid sequence such that the encoded amino acid residue does not change or is another biologically similar residue. In this regard, particularly preferred substitutions will generally be conservative in nature, as described above.

The term "recombinant" means a polynucleotide with semisynthetic, or synthetic origin which either does not occur in nature or is linked to another polynucleotide in an arrangement not found in nature.

"Heterologous" means derived from a genetically distinct entity from the rest of the entity to which it is being compared. For example, a polynucleotide may be placed by genetic engineering techniques into a plasmid or vector derived from a different source, and is a heterologous polynucleotide. A promoter removed from its native coding sequence and operatively linked to a coding sequence other than the native sequence is a heterologous promoter.

The polynucleotides of the invention may comprise additional sequences, such as additional encoding sequences within the same transcription unit, controlling elements such as promoters, ribosome binding sites, 5'UTR, 3'UTR, transcription terminators, polyadenylation sites, additional transcription units under control of the same or a different promoter, sequences that permit cloning, expression, homologous recombination, and transformation of a host cell, and any such construct as may be desirable to provide embodiments of this invention.

Methods of Use and Article of Manufacture

The present invention includes the following method embodiments. In an embodiment, a method of vaccinating an animal comprising administering a composition comprising an *S. suis* strain and a pharmaceutical or veterinarily acceptable carrier, excipient, or vehicle to an animal is disclosed. In one aspect of this embodiment, the animal is a porcine.

In one embodiment of the invention, a prime-boost regimen can be employed, which is comprised of at least one primary administration and at least one booster administration using at least one common polypeptide, antigen, epitope or immunogen. Typically the immunological composition or vaccine used in primary administration is different in nature from those used as a booster. However, it is noted that the same composition can be used as the primary administration and the booster administration. This administration protocol is called "prime-boost".

A prime-boost regimen comprises at least one prime-administration and at least one boost administration using at least one common polypeptide and/or variants or fragments thereof. The vaccine used in prime-administration may be different in nature from those used as a later booster vaccine. The prime-administration may comprise one or more administrations. Similarly, the boost administration may comprise one or more administrations.

The dose volume of compositions for target species that are mammals, e.g., the dose volume of pig or swine compositions, based on bacterial antigens, is generally between about 0.1 to about 2.0 ml, between about 0.1 to about 1.0 ml, and between about 0.5 ml to about 1.0 ml.

The efficacy of the vaccines may be tested about 2 to 4 weeks after the last immunization by challenging animals, such as porcine, with a virulent strain of *S. suis*. Both homologous and heterologous strains are used for challenge to test the efficacy of the vaccine. The animal may be challenged by IM or SC injection, spray, intra-nasally, intra-ocularly, intra-tracheally, and/or orally. Samples from joints, lungs, brain, and/or mouth may be collected before and post-challenge and may be analyzed for the presence of *S. suis*-specific antibody.

The compositions comprising the bacterial strains of the invention used in the prime-boost protocols are contained in a pharmaceutically or veterinary acceptable vehicle, diluent or excipient. The protocols of the invention protect the animal from *S. suis* and/or prevent disease progression in an infected animal.

The various administrations are preferably carried out 1 to 6 weeks apart. Preferred time interval is 3 to 5 weeks, and optimally 4 weeks according to one embodiment, an annual booster is also envisioned. The animals, for example pigs, may be at least 3-4 weeks of age at the time of the first administration.

In another embodiment, the vaccine is administered to a a sow from about 3 weeks to about 6 weeks prefarrowing.

These sows should have reduced reproductive, nursery-age, and growing pig diseases as compared to unvaccinated sows.

It should be understood by one of skill in the art that the disclosure herein is provided by way of example and the present invention is not limited thereto. From the disclosure herein and the knowledge in the art, the skilled artisan can determine the number of administrations, the administration route, and the doses to be used for each injection protocol, without any undue experimentation. Instructions for standard laboratory procedures can be found in many texts and journal articles; see for example, Methods in Molecular Biology, Vol. 66 (Glenn E. Morris, Ed., 1996).

Another embodiment of the invention is a kit for performing a method of eliciting or inducing an immunological or protective response against S. suis in an animal comprising an S. suis immunological composition or vaccine and instructions for performing the method of delivery in an effective amount for eliciting an immune response in the animal.

Another embodiment of the invention is a kit for performing a method of inducing an immunological or protective response against S. suis in an animal comprising a composition or vaccine comprising an S. suis strain of the invention, and instructions for performing the method of delivery in an effective amount for eliciting an immune response in the animal.

Another embodiment of the invention is a kit for detecting the newly discovered strain of S. suis.

Yet another aspect of the present invention relates to a kit for prime-boost vaccination according to the present invention as described above. The kit may comprise at least two vials: a first vial containing a vaccine or composition for the prime-vaccination according to the present invention, and a second vial containing a vaccine or composition for the boost-vaccination according to the present invention. The kit may advantageously contain additional first or second vials for additional prime-vaccinations or additional boost-vaccinations.

The pharmaceutically or veterinarily acceptable carriers or vehicles or excipients are well known to the one skilled in the art. For example, a pharmaceutically or veterinarily acceptable carrier or vehicle or excipient can be a 0.9% NaCl (e.g., saline) solution or a phosphate buffer. Other pharmaceutically or veterinarily acceptable carrier or vehicle or excipients that can be used for methods of this invention include, but are not limited to, poly-(L-glutamate) or polyvinylpyrrolidone. The pharmaceutically or veterinarily acceptable carrier or vehicle or excipients may be any compound or combination of compounds facilitating the administration of the vector (or protein expressed from an inventive vector in vitro); advantageously, the carrier, vehicle or excipient may facilitate transfection and/or improve preservation of the vector (or protein). Doses and dose volumes are herein discussed in the general description and can also be determined by the skilled artisan from this disclosure read in conjunction with the knowledge in the art, without any undue experimentation.

The immunological compositions and vaccines according to the invention may comprise or consist essentially of one or more adjuvants. Suitable adjuvants for use in the practice of the present invention are (1) polymers of acrylic or methacrylic acid, maleic anhydride and alkenyl derivative polymers, (2) immunostimulating sequences (ISS), such as oligodeoxyribonucleotide sequences having one or more non-methylated CpG units (Klinman et al., 1996; WO98/16247), (3) an oil in water emulsion, such as the SPT emulsion described on page 147 of "Vaccine Design, The Subunit and Adjuvant Approach" published by M. Powell, M. Newman, Plenum Press 1995, and the emulsion MF59 described on page 183 of the same work, (4) cationic lipids containing a quaternary ammonium salt, e.g., DDA (5) cytokines, (6) aluminum hydroxide or aluminum phosphate, (7) saponin or (8) other adjuvants discussed in any document cited and incorporated by reference into the instant application, or (9) any combinations or mixtures thereof.

In an embodiment, adjuvants include those which promote improved absorption through mucosal linings. Some examples include MPL, LTK63, toxins, PLG microparticles and several others (Vajdy, M. Immunology and Cell Biology (2004) 82, 617-627). In an embodiment, the adjuvant may be a chitosan (Van der Lubben et al. 2001; Patel et al. 2005; Majithiya et al. 2008; U.S. Pat. No. 5,980,912).

In an embodiment, the adjuvant may be inactivated bacteria, an inactivated virus, fractions of inactivated bacteria, bacterial lipopolysaccharides, bacterial toxins, or derivatives or combinations thereof.

In an embodiment, the adjuvant comprises whole bacteria and/or viruses, including *H. parasuis, clostridium*, swine immunodeficiency virus (SIV), porcine circovirus (PCV), porcine reproductive and respiratory syndrome virus (PRRSV), *Mannhemia, Pasteurella, Histophious, Salmonella, Escherichia coli*, or combinations and/or variations thereof. In several embodiments, the adjuvant increases the animal's production of IgM, IgG, IgA, and/or combinations thereof.

REFERENCES

1. Hill J E, Gottschalk M, Brousseau R, Harel J, Hemmingsen S M, Goh S H. Biochemical analysis, cpn60 and 16S rDNA sequence data indicate that *Streptococcus suis* serotypes 32 and 34, isolated from pigs, are *Streptococcus orisratti*. Vet Microbiol. 2005; 107(1-2):63-9.
2. le Tien H T, Nishibori T, Nishitani Y, Nomoto R, Osawa R. Reappraisal of the taxonomy of *Streptococcus suis* serotypes 20,22,26, and 33 based on DNA-DNA homology and sodA and recN phylogenies. Vet Microbiol. 2013; 162(2-4):842-9.

The invention will now be further described by way of the following non-limiting examples.

EXAMPLES

Example 1—Analysis of a Reproductive Disease Outbreak

Figure 2A:
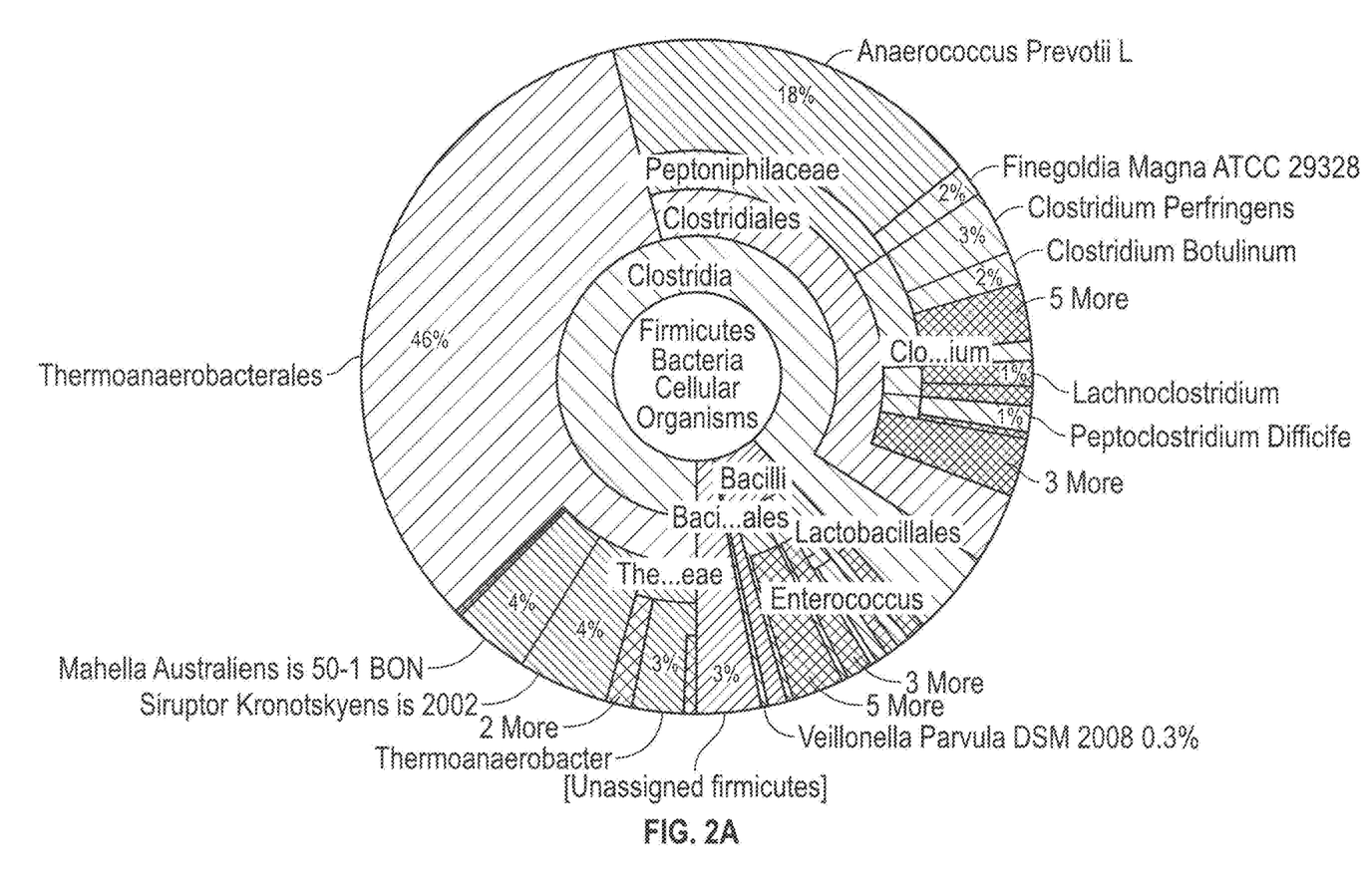
Figure 2B:
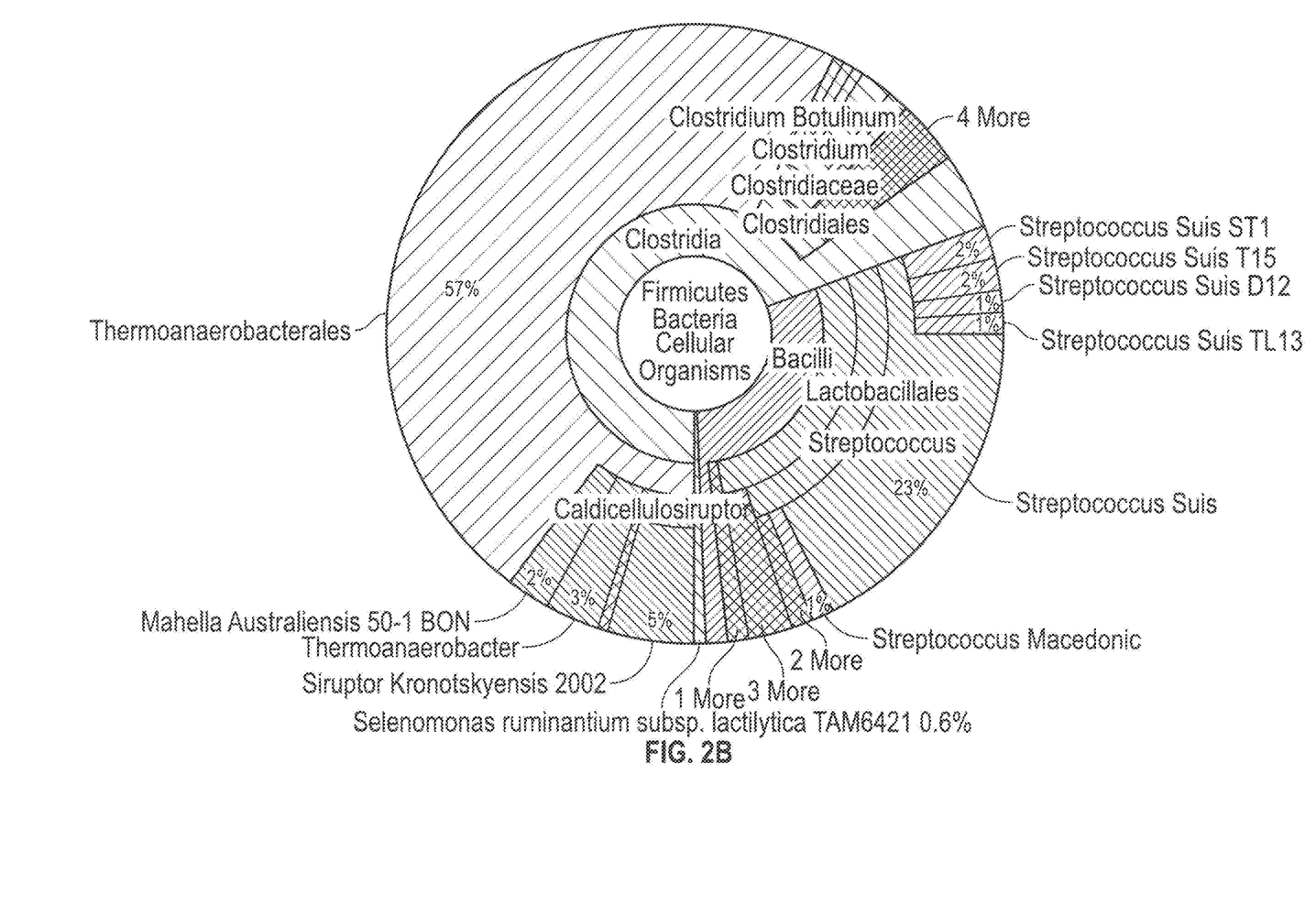

Vaginal swab samples were received as part of an investigation meant to identify the cause of a recent surge in abortions at a farm. Nasal swabs and tissue samples from the same herd were also received. FIG. 2a shows the normal distribution of bacteria in sows. FIG. 2b shows the bacterial distribution in aborting sows with vaginal discharge, noting that several strains of S. suis were isolated from the swab and tissue samples.

Figure 3:
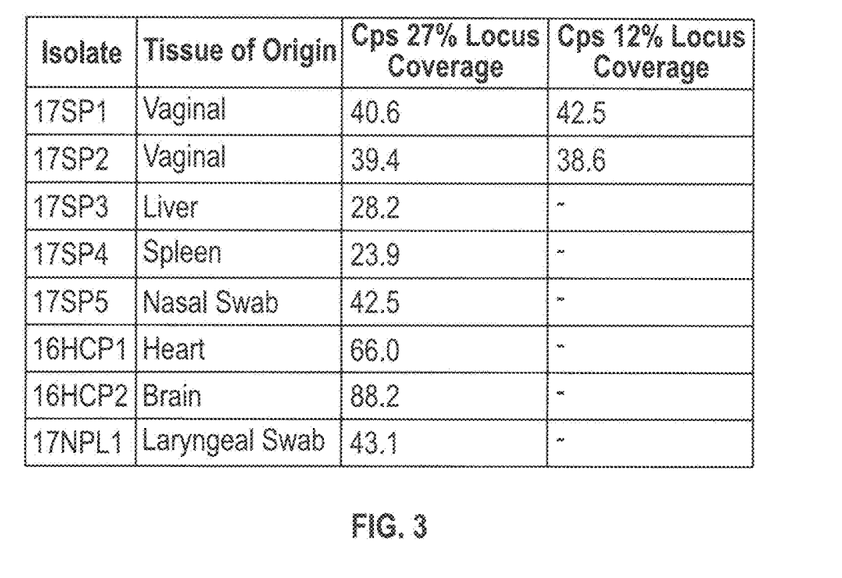
FIG. 3 shows map-based serotyping results from divergent serotype 27 strains used in comparative analysis.

Using a recently developed serotyping method (Lawrence P K: Map-based serotyping of *Streptococcus suis* field isolates for vaccine formulation. AAVLD annual meeting, 2015; aavld.org/assets/2017) many isolates were identified from these samples as highly divergent serotype strains with some similarity to serotypes 27 and 12 (FIG. 3). S. suis was the only pathogen detected that had any association with reproductive disease.

Standard typing methods were not able to definitively determine the cause of the reproductive disease outbreak. Therefore, to determine whether other abortifacient agents were present, a metagenomic analysis on the vaginal swabs and tissue samples was performed.

Example 2—Metagenomic Analysis of the Vaginal Swabs

Variant *S. suis* strains from this case were further analyzed using comparative genomics to identify virulence factors that were unique to the vaginal isolates. Draft genomes were assembled from the *S. suis* strains that had similar serotypes from this case as well as two other strains in the collection that displayed similar serotyping results against serotype 27.

Vaginal swab samples were taken from symptomatic and asymptomatic sows on the same farm and placed in a nucleic acid preservation solution prior to shipping. RNA was extracted from all samples, converted to cDNA, and used for library preparation. Sequencing was performed using a MiSeq instrument using 2×300 bp chemistry. Metagenomic analysis was performed using Kraken after filtering host reads against the *Sus scrofa* genome. Results were visualized using Krona. Each of these steps was carried out according to standard methods known in the art and described in the references. See, for example, Aline, Ines, et al. "Differential Sharing and Distinct Co-Occurrence Networks among Spatially Close Bacterial Microbiota of Bark, Mosses and Lichens-*AGRIS: International Information System for the Agricultural Science and Technology*, Hillsdale, N.J.: B. L. Erlbaum Associated, 1982, 1 Jan. 1970, agris.fao.org/agris-search/search.do?recordID=US201700210871.

Figure 4:
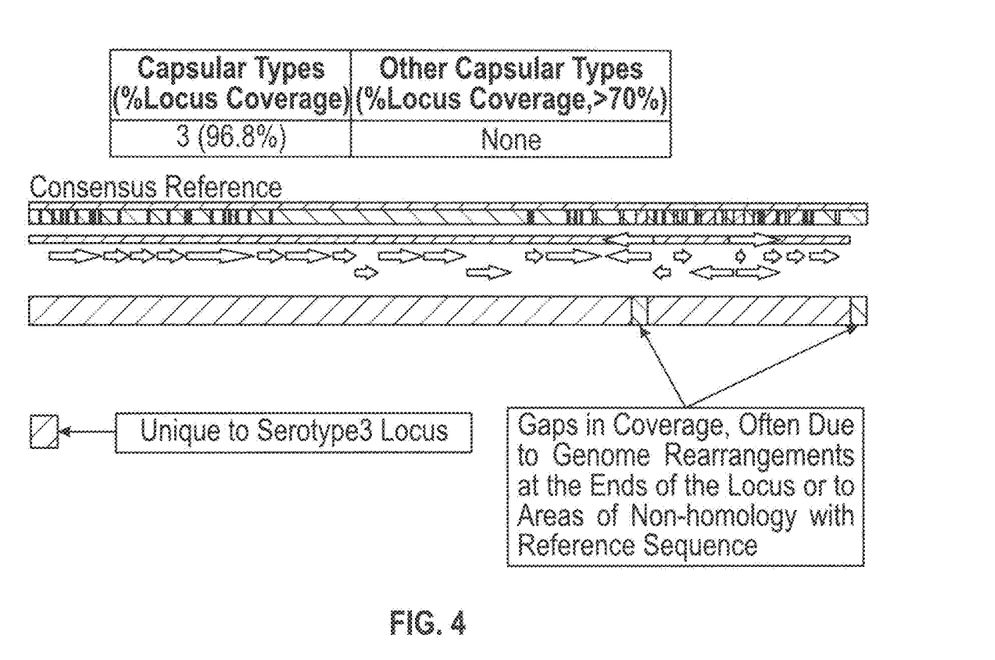
FIG. 4 shows how a simple serotype 3 locus can be inferred based on whole genome sequencing. The solid blue line shows regions unique and similar to serotype 3.
Figure 6:
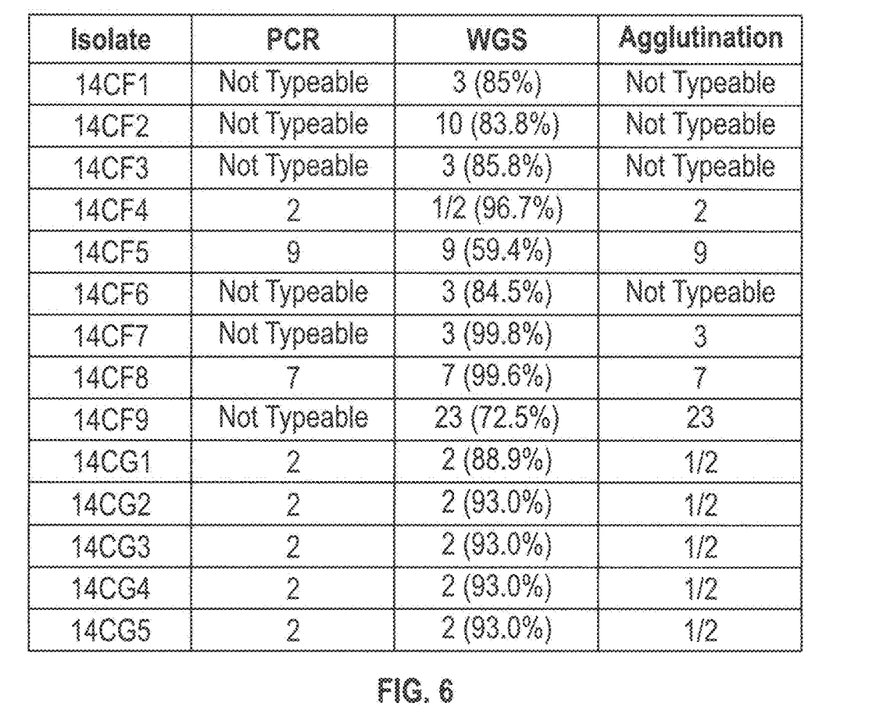
FIG. 6 shows discrepancy between conventional serotyping techniques (PCR, agglutination) versus whole genome sequencing of field isolates.
Figure 7:
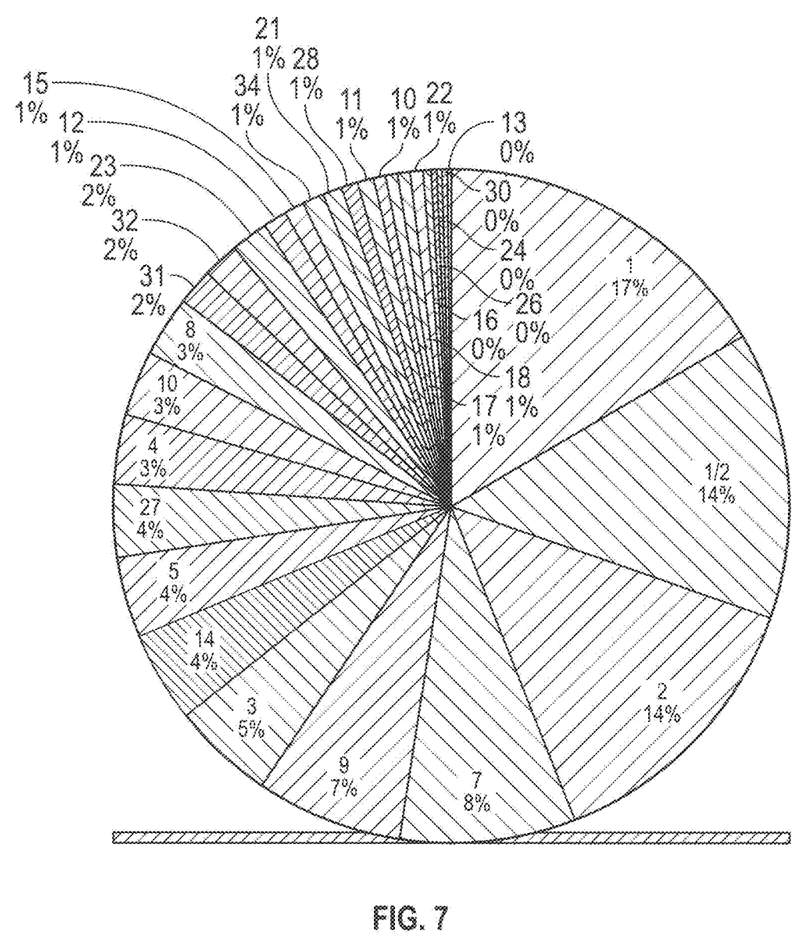
FIG. 7 shows distribution of *Streptococcus suis* serotypes from field samples across the USA (using NPL database).

Following identification of *S. suis* as a potential abortifacient agent, isolates were obtained from different pigs on the same farm site and subjected to serotyping using a previously described method (Lawrence P K, 2015). Genomes were sequenced on a MiSeq instrument using 2×150 bp chemistry and were de novo assembled. Genome comparisons were made amongst all isolates that shared a serotype 27 genotype. These comparisons are shown in FIG. 4, and also in FIGS. 1 and 6.

Figure 1:
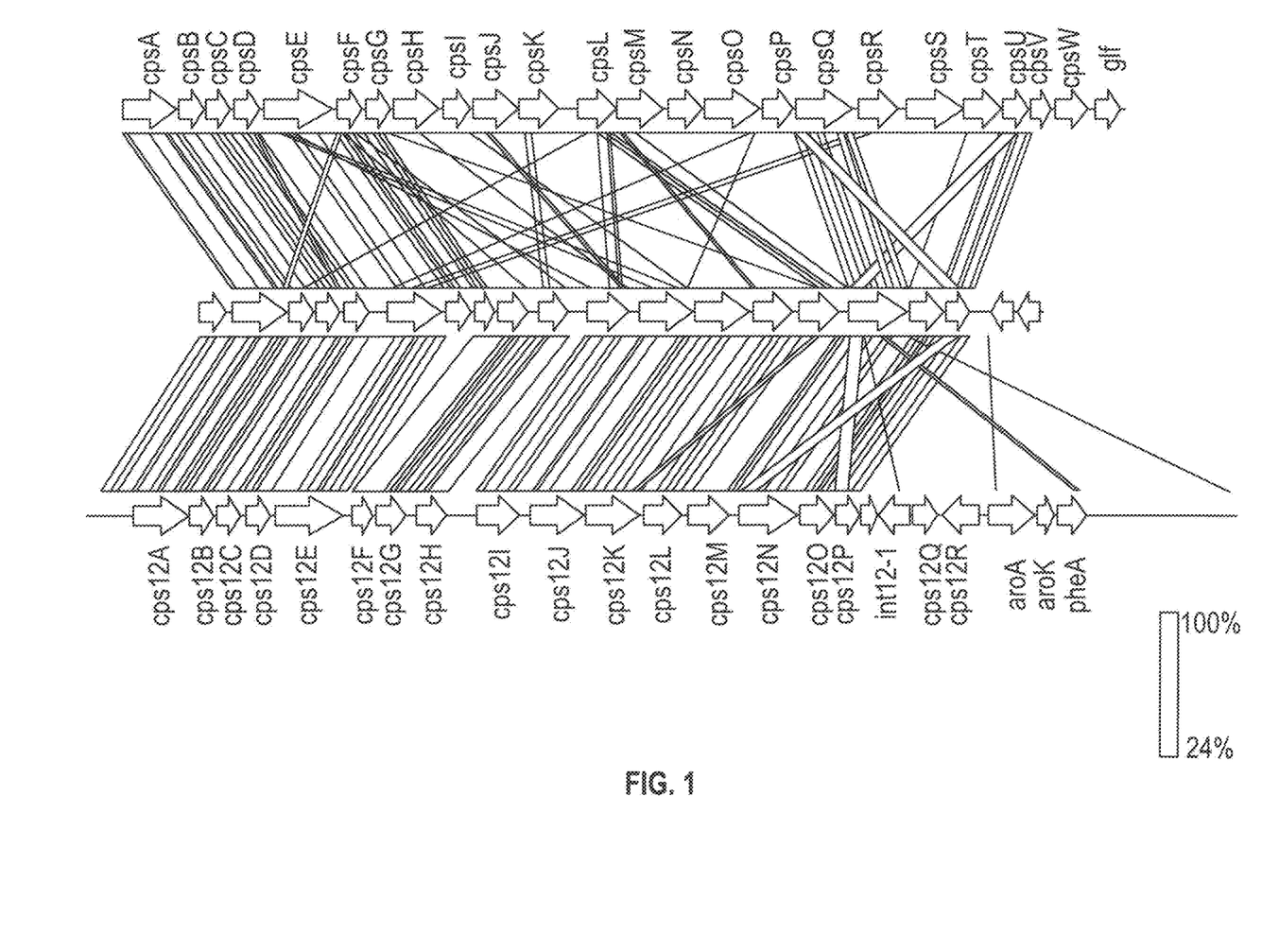
FIG. 1 shows a capsular operon comparison between vaginal swab isolates and Cps operons from YS-149 (novel Cps locus strain) and a Serotype 12 reference strain.

The results obtained from the metagenome samples were surprising; parasitologists would not expect to identify *S. suis* as a possible abortifacient agent in this case. However, there was little else present in the metagenome that could explain the sequelae reported by the veterinarians at this farm site. The comparative analysis initially focused on comparing strains whose closest serotype match was to serotype 27 because a strain with homology to both serotypes 27 and 12 had not been previously isolated. However, the overall structure of the capsular locus in the vaginal isolates was closer to serotype 12. In particular, the cpsN, cpsO, and cpsP genes at the 3' end of the locus are shared between the vaginal isolates and serotypes 12 and 20 (FIG. 1).

Figure 5:
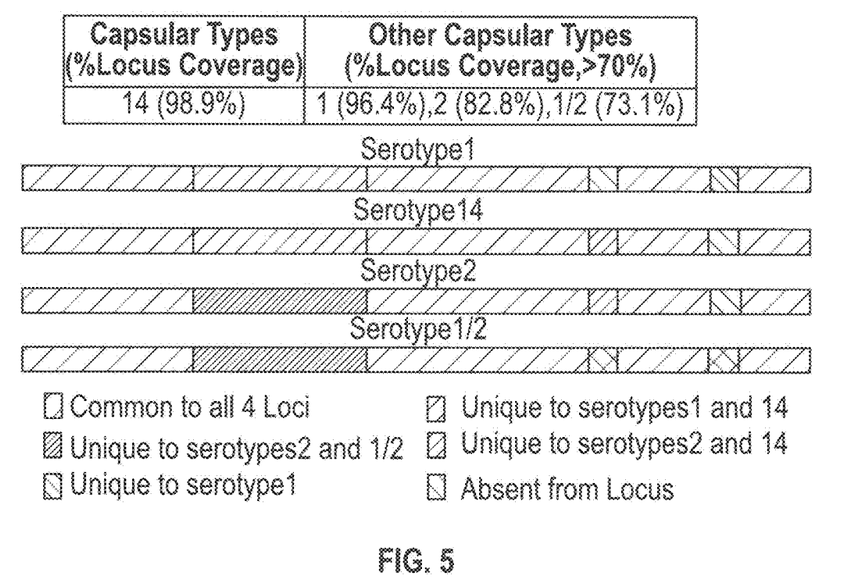
FIG. 5 shows how a complex mosaic capsule structure and CPS loci is inferred based on whole genome sequencing. The capsule region is shared between serotypes 1, 2, ½ and 14. Inferring the correct capsule aids in cross protection.

However, while the cpsN gene from the vaginal isolates bore significant similarity to serotype 12 at the nucleotide level, the cpsO and cpsP genes bore greater similarity to the cpsT and cpsU gens from a previously reported isolate bearing a novel capsule, YS-149 (FIG. 1) (Zheng H, et al.: Eight novel capsular polysaccharide synthesis gene loci identified in nontypeable *Streptococcus suis* isolates. Appl. Environ. Microbiol., 2015, 81:4111-4119). Interestingly, the capsular loci of the vaginal isolates also bears a Fic family protein which they share with YS-149 (cpsF) and serotypes 3, 13, 17, 18, 19, 21, 24, 29, 33 (Okura M, et al.: Genetic analysis of capsular polysaccharide synthesis gene clusters from all serotypes of *Streptococcus suis*: potential mechanisms for generation of capsular variation. Appl Environ Microbial. 2013, 79:2796-2806) but not with serotype 12. Furthermore, the glycosyl transferase and epimerase genes annotated as cpsF and cpsG in serotype 12 are more closely related to serotypes 24 and 21 in the vaginal isolates than to any other serotype (FIG. 5).

Such mosaic structure does not appear to be uncommon amongst *S. suis* isolates since additional strains with novel capsular loci have been reported recently (Pan Z, et al.: Novel variant serotype of *Streptococcus suis* isolated from piglets with meningitis. Appl. Environ. Microbiol., 2015, 81:976-985; Qiu Z, et al.: Novel capsular polysaccharide loci and new diagnostic tools for high-throughput capsular gene typing in *Streptococcus suis*. Appl. Environ. Microbiol., 2016, 21:7102-7112). However, this is the first report in which a particular serotype has been tentatively associated with reproductive disease.

The presence of the alternative secretory pathway in the genome of the vaginal isolates was also an unusual finding. The unique constellation of genes consisting of the novel capsular locus, the alternative secretory pathway, and the cbpD gene may confer upon these strains a unique ability to colonize the vaginal tract. Not only do these genes encode several unique adhesins, but together, they may confer a competitive advantage upon these isolates. Secretion of CbpD in *S. pneumoniae* has been associated with lysis of cells from closely related species (Edholm V, et al.: Fratricide in *Streptococcus pneumoniae*: contributions and role of the cell wall hydrolases CbpD, LytA and LytC. Microbiology., 2009, 155:2223-2234). In *S. pneumoniae*, lytA and lytC were required for efficient target cell lysis in vitro. However, when divalent cations were sequestered using EDTA, lysis was dramatically enhanced using CbpD alone. One might expect that similar conditions would be common in the reproductive tract of infected sows. If CbpD can be exported through the alternative secretory pathway identified herein, then the vaginal isolates might gain an important advantage that could allow them to outcompete other strains present in the reproductive tract.

Thus, the strains appeared to have "alternative forms of genes", which are defined herein as "alleles", relative to their parent *S. suis* strain. In an embodiment, the alternative alleles are responsible for reduced virulence.

Additionally it is believed that two operons contribute to the pathology associated with these strains by serving as host-cell adhesins. The first is an alternative secretory operon. The function of the secretory operon is to export serine-rich repeat glycoproteins to the cell surface where they have been shown to serve as host-cell adhesins. The second operon is a set of capsular genes that are involved in phosphorylcholine metabolism. The capsular genes contributes to the incorporation of phosyphorylcholine into the cell wall, altering capsular structure and allowing for the attachment of choline binding proteins. Choline binding proteins secreted by pathogenic and commensal strains of *Streptococcus* sp. have been implicated as host cell adhesins.

Additionally, the newly identified strains were found to possess a lytic choline binding protein D homolog (cbpD). This protein functions differently in strain with a competent export system.

These findings are shown in the following SEQ ID NOS:
SEQ ID NOS:1 and 2: 1307.1544.peg.724 Beta-1,3-glucosyltransferase [*Streptococcus suis* 17-00802-29] [aSec operon genes] and its translation.

SEQ ID NOS:3 and 4: 1307.1544.peg.723 Nucleotide sugar synthetase-like protein [*Streptococcus suis* 17-00802-29] [aSec operon genes] and its translation.

SEQ ID NOS:5 and 6: 1307.1544.peg.722 Glycosyl transferase, family 8 [*Streptococcus suis* 17-00802-29] [aSec operon genes] and its translation.

SEQ ID NOS:7 and 8: 1307.1544.peg.721 Beta-1,3-glucosyltransferase [*Streptococcus suis* 17-00802-29] [aSec operon genes] and its translation.

SEQ ID NOS:9 and 10: 1307.1544.peg.720 Predicted cell-wall-anchored protein SasA (LPXTG motif) [*Streptococcus suis* 17-00802-29] [aSec operon genes] and its translation.

SEQ ID NO:11 and 12: 11 1307.1544.peg.719 Preprotein translocase SecY2 subunit (TC 3.A.5.1.1) [*Streptococcus suis* 17-00802-29] [aSec operon genes] and its translation.

SEQ ID NOS:13 and 14: 1307.1544.peg.718 Accessory secretory protein Asp1 [*Streptococcus suis* 17-00802-29] [aSec operon genes] and its translation.

SEQ ID NOS:15 and 16: 1307.1544.peg.717 Accessory secretory protein Asp2 [*Streptococcus suis* 17-00802-29] [aSec operon genes] and its translation.

SEQ ID NOS:17 and 18: 1307.1544.peg.716 Accessory secretory protein Asp3 [*Streptococcus suis* 17-00802-29] [aSec operon genes] and its translation.

SEQ ID NOS:19 and 20: 1307.1544.peg.715 Protein export cytoplasm protein SecA2 ATPase RNA helicase (TC 3.A.5.1.1) [*Streptococcus suis* 17-00802-29] [aSec operon genes] and its translation.

SEQ ID NOS:21 and 22: 1307.1544.peg.714 Poly(glycerol-phosphate) alpha-glucosyltransferase GftA (EC 2.4.1.52) [*Streptococcus suis* 17-00802-29] [aSec operon genes] and its translation.

SEQ ID NOS:23 and 24: 1307.1544.peg.713 GftB: Glycosyl transferase, family 8 [*Streptococcus suis* 17-00802-29] [aSec operon genes] and its translation.

SEQ ID NOS:25 and 26: 1307.1544.peg.1161 Choline-phosphate cytidylyltransferase LicC (EC 2.7.7.15)/Choline kinase (EC 2.7.1.32) [*Streptococcus suis* 17-00802-29] [licABC genes] and its translation.

SEQ ID NOS:27 and 28: 1307.1544.peg.1160 Choline permease LicB [*Streptococcus suis* 17-00802-29] [licABC genes] and its translation.

SEQ ID NOS:29 and 30: 1307.1544.peg.1159 Choline-phosphate cytidylyltransferase (EC 2.7.7.15) LicA [*Streptococcus suis* 17-00802-29] [licABC genes] and its translation.

SEQ ID NOS:31 and 32: 17-00802-29_Vaginal_CbpD_real *Streptococcus suis* 17-00802-29 and its translation.

The invention therefore includes methods for preparing and/or formulating immunogenic compositions; e.g., culturing or growing or propagating the bacteria on or in suitable medium, harvesting the bacteria, optionally killing, inactivating or attenuating the bacteria, and optionally admixing the bacteria with a suitable veterinarily or pharmaceutically acceptable carrier, excipient, diluent or vehicle and/or an adjuvant and/or stabilizer. Thus, the invention also relates to the use of the bacteria in formulating such compositions.

Summary: The analysis identified two operons that might contribute to the pathology associated with these strains. The first was an alternative secretory operon and the second was a set of capsular genes that are involved in phosphorylcholine metabolism. The function of the secretory operon is to export serine-rich repeat glycoproteins to the cell surface where they have been shown to serve as host-cell adhesins (Bensing B A, Seepersaud R, Yen Y T, Sullam P M: Selective transport by SecA2: an expanding family of customized motor proteins. Biochim Biophys Acta. 2014, 1843:1674-1686). The capsular genes might contribute to the incorporation of phosyphorylcholine into the cell wall, altering capsular structure and allowing for the attachment of choline binding proteins. Choline binding proteins secreted by pathogenic and commensal strains of *Streptococcus* sp. have been implicated as host cell adhesins (Hakenbeck R, Msfhout A, Denapaite D, Bruckner R: Versatility of choline metabolism and choline-binding proteins in *Streptococcus pneumoniae* and commensal streptococci. FEMS Microbiol Rev., 2009 33:572-586). All of the isolates sequenced possess a lytic choline binding protein D homolog (cbpD) but this protein may function differently in a strain with a potentially competent export system such as the isolated vaginal strains.

FIG. 4 shows how a serotype 3 locus can be inferred based on whole genome sequencing. The solid blue line shows regions unique and similar to serotype 3. Serotype 3 is an example of a simple locus.

Example 3—Development of a New Method of Cellular Typing of *S. suis* that Accurately Identifies all Strains Based on the successful identification described in Example 2, the new method of serotyping is described herein.

The following work flow describes capsule typing based on whole genome sequence (WGS) by way of sequencing and serotyping of isolates. The genomic DNA is extracted and sequenced and the capsule type is derived from the draft genome.

Isolating samples from an infected animal;
extracting genomic DNA;
Purifying genomic DNA;
Preparing libraries for sequencing the genomic DNA;
Sequencing the genomic DNA;
de novo assembling a draft genome; and
Deriving the capsule type from the draft genome by mapping selected gene references to a genomic database.

In this example, the genomic database was derived from the National Center for Biotechnology Information (NCBI, blast.ncbi.nlm.nih.gov/Blast.cgi) and NCBI's GenBank (ncbi.nlm.nih.gov/genbank), and includes additional samples isolated. Additional samples can be found in many public databases, such as the Superfund: National Priorities List (NPL, epa.gov/superfund/superfund-national-priorities-list-npl).

The serotypes identified and used in this example are presented in the following SEQ ID NOS: SEQ ID NO:33 is serotype 1/2 and SEQ ID NOS:34-67 are serotypes 1-34, respectively.

Vaccines and immunogenic agents derived in this manner will provide improved protection against *S. suis* infection compared to other vaccine formulation methods.

Example 4—Vaccine Against the New Strain of *S. suis*

A *Streptococcus* vaccine directed to the new strain of *S. suis* causing disease in reproductive, nursery-age, and growing pigs can be prepared using a polynucleotide selected from the group of SEQ ID NOS: 3, 7, or 11, or a combination thereof, or from a polypeptide that encodes a polypeptide from the sequences selected from the group of SEQ ID NOS: 4, 8, or 12, or a combination thereof.

The vaccine composition may further include a pharmaceutically or veterinary acceptable vehicle, diluent or excipient. It may also include an adjuvant, wherein the adjuvant may be inactivated bacteria, inactivated virus, fractions of inactivated bacteria, bacterial lipopolysaccharides, bacterial toxins, or derivatives or combinations thereof.

Processes and protocols for developing a vaccine are found in patents and publications related to vaccine development, and scholarly articles relating to vaccine development, such as those that can be found in the journal *Vaccines*, journals.elsevier.com/vaccine.

Example 5—Kits for Protecting Against the New Strain of *S. suis*

The invention also includes kits for detecting strains of *S. suis* comprising materials and reagents for collecting samples and materials and reagents for performing a metagenomics analysis.

The invention includes a kit for eliciting or inducing an immunological or protective response against *S. suis* in an animal that doesn't necessarily use a vaccine formulation. For example, simpler methods of exposing animals to an *S. suis* immunological composition may be used, such as methods for aerosol delivery. An amount needed to elicit an immune response can be blown into a nostril. The dosing amount would depend on the age and size of the animal.

The invention also includes kits for prime-boost vaccination comprising at least two vials: a vial containing a vaccine or composition for the prime-vaccination according to the present invention, and a second vial containing a vaccine or composition for the boost-vaccination according to the present invention.

This kit can also include additional vials for additional prime-vaccinations or additional boost-vaccinations.

In conclusion, this study has revealed the presence of a strain of *S. suis* that possesses novel virulence factors and capsular structure in sows exhibiting symptoms of reproductive disease.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

---

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US10968258B2). An electronic copy of the "Sequence Listing" will also be available from the USPTO upon request and payment of the fee set forth in 37 CFR 1.19(b)(3).

---

What is claimed is:

1. An immunogenic composition that elicits an immunogenic response in an animal against *Streptococcus suis* (*S. suis*) infection comprising:
   a) a *S. suis* polynucleotide comprising the sequence of SEQ ID NO: 31; or
   b) a *S. suis* polynucleotide encoding a polypeptide comprising the sequence of SEQ ID NO: 32;
   and wherein the immunogenic composition further comprises a pharmaceutically or veterinary acceptable vehicle, diluent, excipient or adjuvant.

2. The immunogenic composition of claim 1 further comprising at least one additional polynucleotide encoding a polypeptide having an amino acid sequence selected from the group consisting SEQ ID NOs: 4, 8, 12, or combinations thereof.

3. A kit for prime-boost administration comprising at least two vials: a first vial containing the immunogenic composition of claim 1 for the prime-administration, and a second vial containing a composition of claim 2.

4. The kit of claim 3 further comprising additional first or second vials for addition prime-administrations or additional boost-administrations.

5. A method comprising administering at least once to a porcine animal an immunogenic composition of claim 2.

6. A kit for prime-boost vaccination comprising at least two vials: a first vial containing the immunogenic composition of claim 2 for the prime-vaccination, and a second vial containing a different vaccine or immunogenic composition of claim 3 for the boost-vaccination.

7. A method comprising administering at least once to a porcine animal the immunogenic composition of claim 1.

8. The method of claim 7 wherein the porcine is a sow that is about 3 weeks to about 6 weeks prefarrowing.

9. A kit for eliciting or inducing an immunological response against *S. suis* in an animal comprising:
   an *S. suis* immunological composition comprising
      a) a *S. suis* polynucleotide comprising the sequence of SEQ ID 31; or
      b) a *S. suis* polynucleotide encoding a polypeptide comprising the sequence as set forth in SEQ ID NO:32;
   and wherein the immunological composition further comprising a pharmaceutically or veterinary acceptable vehicle, diluent, excipient or adjuvant;
   and instructions for performing the method of delivery an effective amount for eliciting an immune response in the animal.

10. The kit of claim 9 wherein the immunological composition further comprises at least one additional polynucleotide encoding a polypeptide selected from the group consisting of SEQ ID NOs: 4, 8, 12, or combinations thereof.

* * * * *

UNITED STATES PATENT AND TRADEMARK OFFICE
CERTIFICATE OF CORRECTION

PATENT NO. : 10,968,258 B2
APPLICATION NO. : 16/118857
DATED : April 6, 2021
INVENTOR(S) : Paulraj Lawrence Page 1 of 1

It is certified that error appears in the above-identified patent and that said Letters Patent is hereby corrected as shown below:

On the Title Page

Item (56) References Cited page 2 'accession No. WP_044766479' should read --WP_044768479--.

In the Claims

Claim 2 (Column 17, Line 52) 'the group consisting SEQ ID NOs: 4, 8, 12, or combinations' should read --the group consisting of SEQ ID NOs: 4, 8, and 12, or combinations--.

Claim 3 (Column 17, Line 55) 'containing the immunogenic' should read --containing an immunogenic'--.

Claim 3 (Column 17, Line 57) 'containing a composition' should read --containing an immunogenic composition--.

Claim 4 (Column 17, Line 59) 'vials for addition' should read --vials for additional--.

Claim 6 (Column 18, Line 41) 'of claim 3' should read --of claim 2--.

Claim 9 (Column 18, Line 48) 'an' should read --a--.

Claim 9 (Column 18, Line 50) 'SEQ ID: 31; or' should read --SEQ ID NO: 31; or--.

Claim 9 (Column 18, Lines 54-55) 'further comprising' should read --further comprises--.

Claim 10 (Column 18, Line 63) 'SEQ ID NOs: 4, 8, 12, or combinations' should read --SEQ ID NOs: 4, 8, and 12, or combinations--.

Signed and Sealed this
Twenty-third Day of May, 2023

Katherine Kelly Vidal
*Director of the United States Patent and Trademark Office*